United States Patent [19]
Fry et al.

[11] Patent Number: 5,827,562
[45] Date of Patent: Oct. 27, 1998

[54] SWEETENER SALTS

[75] Inventors: John C. Fry, Meerssen; Jacob Van Soolingen, Brunssum, both of Netherlands

[73] Assignee: Holland Sweetener Company V.o.F., Maastricht, Netherlands

[21] Appl. No.: 728,594

[22] Filed: Oct. 10, 1996

Related U.S. Application Data

[60] Provisional application No. 60/007,780, Nov. 30, 1995.

[30] Foreign Application Priority Data

Oct. 11, 1995 [BE] Belgium ............................. 09500836

[51] Int. Cl.⁶ ............................. A23L 1/236; A23L 1/216; C07C 261/00; C07C 229/00
[52] U.S. Cl. ............................. 426/548; 426/804; 426/96; 426/291; 560/24; 560/25; 560/41
[58] Field of Search ................................... 426/548, 804, 426/96, 291; 560/24, 25, 41

[56] References Cited

U.S. PATENT DOCUMENTS

| | | | |
|---|---|---|---|
| 3,922,369 | 11/1975 | Glicksman et al. | 426/548 |
| 4,439,460 | 3/1984 | Tsau et al. | 426/548 |
| 4,495,170 | 1/1985 | Beyts et al. | 424/48 |
| 5,114,726 | 5/1992 | Tsau et al. | 426/289 |
| 5,126,158 | 6/1992 | Sharkasi et al. | 426/548 |
| 5,164,214 | 11/1992 | Wild | 426/548 |

FOREIGN PATENT DOCUMENTS

| | | |
|---|---|---|
| 1027113 | 2/1978 | Canada . |
| 0 140 517 A2 | 5/1985 | European Pat. Off. . |
| 8604766 | 7/1986 | Spain . |

*Primary Examiner*—Marian C. Knode
*Assistant Examiner*—Ali R. Salimi
*Attorney, Agent, or Firm*—Pillsbury, Madison & Sutro LLP Cushman, Darby & Cushman IP Group

[57] ABSTRACT

The process of the present invention is conducted in a liquid medium and concerns the preparation of a sweetening salt as the reaction product from two sweetener components in which one component is a sweetener derived from aspartic acid and the other is an intense sweetener not derived from aspartic acid. The process steps include adding to a liquid medium, in any order, a sweetener derived from aspartic acid, a derivative, such as a salt, of a sweetening acid not derived from aspartic acid, and a strong acid whereby a liquid system is obtained, allowing the components then present in the liquid system to react for at least one minute such that the sweetening salt formed, and isolating the sweetening salt. Novel sweetening salts having a good thermal stability and a low moisture content, as well as a new crystal modification of the sweetening salt from aspartame and acesulfamic acid are also disclosed. The sweetening salts can be used in foodstuff and the like.

34 Claims, 2 Drawing Sheets

SWEETENER SALTS

BACKGROUND OF THE INVENTION

1. Field of the Invention

The present invention relates to a process for the preparation of sweetening salts which consist of two sweetener components. In particular, the present invention relates to the preparation of sweetening salts in a liquid medium. The sweetening salts are formed starting from two sweetener components, one of which is a sweetener component derived from aspartic acid and the other from is a derivative of an organic sweetening acid which corresponds to an intense sweetener not derived from aspartic acid. The present invention also relates to new sweetening salts which have good thermal stability and a low moisture content. The present invention further relates to a new crystal modification of the sweetening salt from aspartame and acesulfamic acid. In addition, the invention relates to the application of sweetening salts in foodstuff compositions, confectionery, sweets, chewing gum, etc. The invention further relates to preparations of such sweetening salts.

2. Related Art

ES-A-8604766 discloses such a process for the preparation of, for example, salts of the aspartic acid derived sweetener aspartame (Δ-L-aspartyl-L-phenylalanine methyl ester; hereinafter also referred to as APM) and saccharinic acid (3-oxo-2,3-dihydro-1,2-benzisothiazole-1,1-dioxide). ES-A-8604766 also mentions acesulfamic acid and glycyrrhizic acid as potential starting materials. However the disclosed process finds limited applicability, and thus is not susceptible to general use in preparing sweetening salts. Namely according to this publication, the only derivative of an organic sweetening acid for which process in practice has been carried out is saccharinic acid itself, is dissolved in methanol, and thereafter a quantity of aspartame that is equimolar to the acid is added. Then, the mixture is heated to 40°–50° C. until a solution is obtained. The solution is subsequently evaporated using the rotavapor, until a solid has formed or up to a predetermined concentration, and the salt formed can be recovered, optionally by addition of a methanol-miscible organic solvent. This salt recovery can be done either by separation as an insoluble product or by recovery in the solvent added or in the solvent system obtained. The main disadvantage of this process is that the organic acid must be used. The applicability of this method is consequently essentially limited to the preparation of saccharinates, because since eligible organic sweetening acids other than saccharinic acid generally have an unstable character and are therefore hard to obtain. For that matter, we have also discovered that poor results are obtained when the process described in ES-A-8604766 is carried out using an organic sweetening acid other than saccharinic acid in a manner analogous to the preparation of the products from saccharinic acid. So far no other suitable processes for the preparation of such other salts are known. In addition, as explained in the experimental part of the present application, we have also discovered that the salts obtained according to the process of ES-A-8604766 have a relatively high moisture content and limited thermal stability. This is particularly true for when a salt of aspartame and acesulfamic acid is prepared in a manner analogous to the process of ES-A-8604766.

At this time, a great number of intensive sweeteners are known. A substantial number of these are derived from aspartic acid. Aspartame (Δ-L-aspartyl-L-phenylalanine methyl ester; APM), for example, now is one of the most important intense sweeteners. APM's sweetening power is about 200 times that of sugar. Examples of other sweeteners derived from aspartic acid are compounds such as the APM-corresponding lower alkyl esters, esters of L-aspartyl-D-serine and L-aspartyl-D-threonine (Aryoshi et al., Bull. Chem. Soc. Jap., 47, 326 (1974)), esters of L-aspartyl-D-alaninol and L-aspartyl-D-serinol (U.S.-A-3,971,822), 3-L-α-aspartyl-D-alanylamido-2,2,4,4-tetramethylthietanylamine (alitame; EP-A-0034876; approx. 2000× the sweetening power of sugar), and many others.

In addition, various other synthetic intense sweeteners are known which are derived not from aspartic acid but from other organic acids. In this patent application these are referred to as organic sweetening acids. Examples are the long-known sweeteners acesulfame-K (6-methyl- ,2,3-oxathiazin-4(3K)-one-2,2-dioxide; hereinafter also referred to as AceK; 200× sugar; U.S.-A-3,689,486), saccharin-Na (sodium 2,3-dihydro-3-oxobenzisosulfonazole; 300× sugar) and cyclamate-Na (sodium cyclohexylsulfamate; 30× sugar). In particular, the sodium, calcium and potassium salts of the relevant acids have been proven to have suitable sweetening properties. These sweeteners, too, just like APM, are used in large quantities for sweetening of foodstuffs such as soft drinks, diet products, chewing gums, confectionery, sweets, etc. The organic sweetening acids themselves are less suitable as sweeteners per se because they are either unstable or exhibit a less suitable taste profile. Moreover, the organic sweetening acids are only slightly water-soluble.

It should be noted that th e possibilities of using intense sweeteners in the various products may be restricted as a consequence of chemical and/or thermal instability aspects during the preparation and/or storage of (end) products containing such sweeteners. Thermal stability of sweeteners, for example, will be an important criterion governing the choice of a sweetener for use in confectionery products. For example, the use of aspartame or its derivatives in such applications is limited due to their relatively unfavorable thermal stability. In this context, U.S. Pat. No. 4,439,460 discloses at column 1, line 30 and following that disadvantageously the then known aspartame salts generally had insufficient thermal stability which rendered them unsuitable for universal application. Consequently, it was concluded that only specific sulphate ($SO_4^-$) and organosulphate ($RSO_3^-$) salts of aspartame had sufficient thermal stability.

ES-A-8604766 does mention that salts on the basis of two intense sweetener components may have (synergistic) sweetening properties without—in solid form or dissolved—the bitter taste of the acid being noticed, as well as advantages in terms of dissolution rate, etc., but apparently such salts have so far hardly found practical application due to their limited accessibility and their limited thermal stability.

Therefore a need remains for a more universal, facile process for the preparation of sweetening salts consisting of two sweetener components. In particular, there has been a need for a process for preparing a sweetener derived from aspartic acid and an organic acid corresponding to an intense sweetener that is not derived from aspartic acid. A further long-existing need in the art has been for sweetening salts in a thermally stable form which have a low moisture content without the above-mentioned drawbacks, and relatedly for such salts which are not restricted to being prepared based on the organic acid in question.

SUMMARY AND OBJECTS OF THE INVENTION

Surprisingly, we have discovered that sweetening salts consisting of two sweetener components can be prepared in a very suitable manner in a liquid medium and that the obtained sweetening salts are in a thermally stable form, and have a low moisture content.

Our discovery includes a method comprising the combination of steps of (a) forming a liquid system containing a sweetening salt of a sweetener derived from aspartic acid and a sweetener component derived from an organic sweetening acid which corresponds to an intense sweetener not derived from aspartic acid by adding to a liquid medium, in any order, components (i), (ii) and (iii):
  (i) the sweetener derived from aspartic acid,
  (ii) a derivative (salt) of an organic sweetening acid which corresponds to an intense sweetener not derived from aspartic acid, and
  (iii) a strong acid;

b) allowing the components then present in the system (liquid medium plus components), optionally with agitation, to react for at least one minute, wherein a reaction mixture containing the sweetening salt is formed; and c) isolating the sweetening salt from the reaction mixture so obtained.

DETAILED DESCRIPTION OF THE INVENTION

Our method is a universally applicable and simple one for preparing the desired sweetening salts without the disadvantages inherent in the instability of most of the relevant organic sweetening acids that could be used as starting products.

Elsewhere herein we have included a non-exhaustive list of sweeteners derived from aspartic acid that can be used as starting product in the framework of this invention. These substances are conveniently referred to as component (i) or starting material (i) in the application. By special preference, aspartame and alitame are used as starting material (i) from this group of compounds, because according to the present invention, the products derived from them have good properties in terms of taste, low moisture content and thermal stability.

Elsewhere herein we have also included a non-exhaustive list of (salts of) organic sweetening acids, corresponding to intense sweeteners not derived from aspartic acid, that can be used as starting materials in the present invention. These substances will conveniently be referred to as component (ii) or starting material (ii). The salts of the organic sweetening acid are preferably selected from the group formed by potassium, sodium, calcium, ammonium, secondary amine or tertiary amine salts of the organic sweetening acid. Particularly suitable starting materials (ii) are the relevant salts of organic acids selected from acesulfamic acid, saccharinic acid or cyclamic acid.

The starting materials (i) and (ii) do not have to be used in dry or virtually dry form. Thus, for example, it is possible to use a wet crystal mass obtained in processes for the preparation of the sweetener derived from aspartic acid, for example a 2–6 wt.% APM slurry in water, or a wet APM crystal cake with a moisture content, for example, of 30–70 wt.% that is obtained in a further process step after solid/liquid separation using centrifuges or another separation technique. It is also possible to use aqueous suspensions containing a dispersing agent, for example a 10–70 wt.% suspension of APM in water, such as the commercially available NutraSweet Custom Liquid®, as starting material.

In principle, the process according to the present invention can be carried out in any liquid medium. As will be evident to those skilled in the art, the liquid medium is inert relative to (that is, does not react irreversibly with) both the starting materials and the products to be obtained. The term liquid medium therefore means any medium that is inert relative to the reagents (the components (i) and (ii) used as starting materials), the end product and the strong acid (iii). The medium is liquid at the selected process temperature range. The term slurry is used, if during one or more steps of the process and depending on the liquid medium selected, a solid is present in the liquid medium. The solid present may consist of one or more of the starting materials (i) and (ii) and/or the desired sweetening salt or inorganic salt formed during the process. In many cases a slurry will be present in the process according to the present invention. This is not an impediment to practicing our process. It is even advantageous if at least 1.0 wt.% of solid material is present in the reaction mixture after step (b), i.e. a slurry with at least 1.0 wt% of solid material. Usually, therefore, such a slurry has a solids content of at least 1.0 wt.% relative to the weight of the total of liquid medium and starting materials and strong acid. However, higher solids contents are quite possible. The slurry can, for example, have a solids content of up to, for example, 50 wt.% or even 60 wt.% relative to the weight of the total of liquid medium and starting materials used and strong acid, without agitation of the system becoming impossible. An exact upper limit for the solids content can therefore hardly be indicated. It is determined by practical considerations relating to the stirrability and viscosity of the system, during and at the end of the process. The solids content can thus be easily be established by one skilled in the art. The stirrability of the system can, if desired, be improved by adding a dispersing agent, for example hexaethyl cellulose (HEC). Depending on the liquid medium and the process conditions that have been selected, the process according to the invention can also be carried out fully or largely in solution, i.e. without the presence of solid(s).

However, in view of the higher volume yields that can be achieved and the higher purity of the end product, the process is preferably carried out under such conditions that at least 1.0 wt.% of solid material is present in the reaction system, if desired, already before the acid component (iii) addition to the liquid medium in step (a). It is certainly preferred that at least 110 wt % of solid material is present in the reaction system by the end of step (b). The solid does not necessarily have to be the desired sweetening salt itself but may, depending on the liquid medium selected, also be an inorganic salt.

For practical and economic reasons the liquid medium is selected from among water, less or more polar organic solvents, such as, for example, lower alcohols (with 1–8 carbon atoms) or ketones, such as for example acetone or methylisobutylketone (MIBK) or halogenated hydrocarbons with 1–6 carbon atoms, or esters (e.g. ethyl acetate), or ethers, such as, for example, methyl-t-butylether (MTBE), dibutyl ether, diethyl ether and tetrahydrofuran, and apolar organic solvents such as alkanes (e.g. pentane., hexane, cyclohexane, petroleum ether), aromatics (e.g. toluene or benzene), as well as water-miscible or water-immiscible solvents, such as for example solutions, mixed in suitable proportions, of methanol and methylethylketone (MEK), MIBK or MTBE, or other mixtures with components from the above-mentioned liquids, including aqueous media. If the liquid medium contains a substantial quantity of water, for example at least 50% of the total weight of the liquid medium, it is referred to as an aqueous medium in the framework of this invention. The liquid medium may, if desired, already include a quantity of the strong acid, component (iii).

An aqueous medium is preferably used as the liquid medium. On the one hand, an aqueous medium is preferable when alkali (alkaline earth) metal salts of the organic sweetening acid are used because the inorganic salt present at the end of the process then remains in solution whereas the desired sweetening salt can be recovered directly as a solid from the aqueous medium. When the process according to the invention is carried out in an aqueous medium, a slurry is generally already obtained after addition of component (i), and mostly solids will also be present at the end of the process. Therefore, the process can usually also be called a "slurry conversion" process when conducted in an aqueous medium. According to the present invention, when the conversion is carried out in, for example, (m)ethanol, an inorganic salt precipitates at the end of process whereas, in general, the sweetening salt which forms remains in solution. In this case the process can also be called a "slurry conversion" process. In more general terms, the process can also be referred to as a "trans-salification process" that makes it clear that processes according to the present invention also encompass ones which are conducted under conditions, such as the liquid medium selected et cetera, that the desired sweetening salt remains in solution and which is conducted wholly or largely in the absence of solids.

In step (c) the desired sweetening salt is isolated from the reaction mixture by solid-liquid separation. If the sweetening salt itself is present as a solid at the end of step (b), the solid-liquid separation can be carried out directly. The reaction mixture can, if desired, be concentrated to some extent by partially evaporating the liquid medium, preferably at reduced pressure, before effecting a solid-liquid separation. If, for example, the sweetening salt, is prepared in (m)ethanol as the liquid medium and is present in solution at the end of step (b) and if an inorganic salt is present as a solid, the inorganic salt can first be removed by solid-liquid separation, and then the sweetening salt can be crystallized out of the filtrate by cooling or by adding a second liquid medium, optionally in combination with complete removal of liquid medium (e.g. through spray drying) or with a concentration step in which the solution is partly evaporated until a precipitate has formed. The sweetening salt then precipitated is subsequently recovered by solid-liquid separation. The sweetening salt obtained can, if desired, be dried further. In all cases, therefore, selective crystallization of the sweetening salt can basically be said to take place.

Removal of all or part of the inorganic salt formed in the slurry conversion process is not necessary for the process according to the invention. Through a suitable choice of the liquid medium, such that in this medium both the solubility of the sweetening salt formed and that of the inorganic salt being formed are relatively high, even at temperatures of 20° C. to 40° C., the reaction mixture obtained can—most expediently—be used directly in, for example, a spray-drying process. A relatively high solubility of both the sweetening salts and the inorganic salt formed can be achieved by using mixed solvent combinations, such as for example water/(m)ethanol systems with a high (m)ethanol content, for example about 60 to about 95% (v/v). One skilled in the art can easily determine under what conditions a spray-drying process can suitably be carried out without (prior or intermediate) removal of the inorganic salt.

On the other hand, an aqueous medium is the preferred liquid medium because the sweetening salts, then obtained is used have the best properties. This is particularly so with respect to low moisture content and thermal stability. The most preferred aqueous medium is water itself because, for instance, large crystals can be obtained using such a medium. Large crystals are advantageous in the solid-liquid separation. As will be explained below, when the present process is carried out with water as liquid medium, the sweetening salt of aspartame and acesulfamic acid is obtained in a new, highly suitable crystal modification. In addition, water is particularly suitable as liquid medium because, apart from minute quantities of liquid, no organic solvent residues are present in the end product. The present process can, however, be suitably carried out both in an aqueous medium and in a medium having a more organic nature when amine salts or ammonium salts of the organic acid are used as starting material.

The concentrations of the quantities of components (i) and (ii) in the liquid system are not critical and can vary within very wide limits. Higher concentrations are preferred for reasons of economy, also in case solid material is present in the system. Suitable concentrations include, for example, more than 10 wt.%, and more preferably 30–50 wt.%, or even higher concentrations, for example, 60 wt.%. Moreover, it is self-evident that the highest possible concentrations are preferred not only in a so-called "slurry conversion" process, but also when the process is wholly or largely carried out in solution when the appropriate liquid medium and process temperature are selected.

The molar ratio between the starting materials (i) and (ii) in the process according to the invention can generally be varied within wide limits. The molar ratio of substances (i) and (ii) can generally be in a range from 0.2:1 to 5:1, but is more preferably in a range from 0.5:1 to 2:1. A sweetening salt in solid form which virtually purely consists of the 1:1 salt of the sweetener derived from aspartic acid and the organic sweetening acid is obtainable when practicing the process within these ranges in combination with a suitable choice of combinations of starting materials (i) and (ii), strong acid, liquid medium and other process conditions. The 1:1 salt is still mostly obtained even if molar ratios of components (i) and (ii) deviate from 1:1, when the liquid medium is obtained so that either the component (i) or (ii) remaining at the end of the process, which was the starting material that was present in an excess, remains in solution and the sweetening salt is present as precipitate; or the sweetening salt remains in solution while the component (i) or (ii) that is present in an excess is present as a solid. The former results, for example, in an aqueous environment; and the latter results, for example, in (m)ethanol.

The quantities of components (i), (ii) and (iii) are preferably selected so that the product eventually obtained, i.e. the sweetening salt, consists substantially, i.e. to at least 90 wt.%, in particular at least 95%, based on the dry weight, of the desired sweetening salt. The presence of inorganic salt, even in quantities of up to about 15 wt.% relative to the sweetening salt, is not considered to cause any interference.

The molar ratio between the starting materials (i) and (ii) is preferably 1:1 because of the stoichiometry of salt formation and process economy. If desired, one skilled in the art can create a final solid product having a very special taste or stability profile by suitably selecting the quantities used and the molar ratio between components (i) and (ii) as well as, of the strong acid, and obtain a sweetening salt in solid form as a desired product which remains at the end of the process, but which also includes a part of one of the components (i) or (ii) in solid form.

The effects to be achieved through the attempts to secure the presence of an excess of starting material in the end product are not identical with, but can perhaps best be compared to, the effects obtained by combining various sweeteners in certain quantities. The use of combinations (blends) of intense sweeteners (which may lead to, for example, mutual reinforcement of the sweetening power (synergy)), or with other components, in order to improve the taste profile or to eliminate a bitter aftertaste or other undesirable phenomena, is known. Combinations of such sweeteners can generally be obtained through mixing of the individual components. A major disadvantage of such combinations of sweeteners is that—in solid form—demixing, i.e. separation of the different solid sweeteners, may take place.

Where this application refers to agitation, what is meant is that the system is at least partly kept in motion, for example by stirring or shaking, so that a relatively homogeneous distribution of the various components that are present is achieved while preventing too high, undesirable local concentrations of the strong acid (iii) which may give rise to undesirable side-reactions, such as hydrolysis. However, there is no need for very strong agitation. Its magnitude is also determined by the thickness and the stirrability of the slurry that may be present at any moment during the process. In generally, only little agitation is required. Good results are still possible even without agitation, perhaps because the crystallization taking place during trans-salification during the process, proceeds even better in the absence of agitation. The crystallization results are, in particular, good in the absence of agitation when the process is carried out in an aqueous medium. In particular, there is no or hardly any need for agitation when the strong acid (iii) is dosed gradually. Moreover, if a slurry is present, sudden thickening of the slurry is found to occur upon fast addition of the strong acid (iii), which also makes it difficult to stir the slurry.

Trans-salification according to the present process generally proceeds relatively fast. In principle, it is enough to allow the components to react in step (b), even at room temperature, for at least one minute to achieve full conversion. This also holds true when the process proceeds as a "slurry conversion" reaction.

Suitable strong acids (iii) useful in practicing the present invention are generally organic or inorganic acids having a $pK_a$ that is lower than the $pK_a$ of the sweetener derived from aspartic acid (component (i)). However, they are preferably selected from among hydrochloric acid, sulphuric acid or phosphoric acid. The strong acid used as component (iii) can be applied in the form of a solution of the strong acid in a liquid medium as used in the framework of the subject process. That solution can be dilute or strongly concentrated. In particular, the strong acid is used as a solution in the same liquid medium as used in the process applied. If hydrochloric acid is used as strong acid, it can be added by introducing gaseous HCl.

At least a portion of the strong acid (iii) is added to the liquid medium in step (a), but further addition can also take place, preferably gradually, during step (b).

The quantity of strong acid to be used in step (a) where optionally a portion of the strong acid may even be present already in the liquid medium, and in step (b), where addition of the strong acid preferably takes place gradually, is not very critical. The quantity can be varied within broad limits, and in general amounts to least 25% (in $H^+$equivalents) of the quantity of component (i). If the total quantity of the strong acid used is less than equivalent (in $H^+$equivalents) relative to the sweetener derived from aspartic acid (component (i)), then 100% conversion of the latter substance into the desired sweetening salt will not be possible, so that part of the latter substance may remain present in the end product as a solid in addition to the solid sweetening salt that has been formed.

There are no objections to the quantity of strong acid (iii) being more than 100% (in $H^+$equivalents) of the quantity of component (i). The excess strong acid then present generally remains behind in solution. However, the quantity of strong acid selected is not too high in order to avoid decreasing the pH of the reaction system to a level whereby undesirable side reactions, such as hydrolysis, take place. If the total quantity used of the strong acid (iii) is greater than equivalent (in $H^+$equivalents) relative to the sweetener derived from aspartic acid, this will be less acceptable from an economic point of view. Unnecessarily high consumption of strong acid and the need for neutralizations, et cetera, in any further process steps can result. If the presence of any residual AceK in the resulting solid product is deemed undesirable, then a quantity of strong acid (in $H^+$equivalents) of at least equivalent to the quantity of Acek is preferably used. For example, residual Acek may be undesired from the perspective of a taste profile, when, for example, an acesulfame salt excess (e.g. AceK) relative to APM is used in the preparation of the aspartame-acesulfame salt. As already explained, this partly depends on the liquid medium that has been selected.

The order in which each of the components (i), (ii) and strong acid (iii) are dosed does not prove to be critical. Any order of dosing to the liquid medium can be selected, without any substantial effect on the product obtained. It is, however, recommended to dose one of the three components (i), (ii) and (iii), and preferably the strong acid (iii), to the other components after these have been added to the liquid medium. Optionally, two of the three components may be added simultaneously to the liquid medium by, for example, in the preparation of the aspartame-acesulfamic acid salt, simultaneously adding the aspartame and the strong acid, or alternatively acesulfame-K and the strong acid. In the latter case this can be done both separately and in the form of a mixture. Addition of the component(s) not yet present preferably takes place gradually.

Where this application refers to gradual addition of one or more of the components in one or more of the process steps (a)–(c), this means that the component(s) is (are) added slowly, for example in 5 minutes to 2 hours, continuously or in small portions, to the system, depending on the concentration in the system and the total quantities to be added. This is of particular importance with respect to the strong acid (iii) addition. Where too high local concentration of the strong acid are undesirable. This can simply be determined through optimization by one skilled in the art.

In a particularly suitable embodiment of the present process, components (i) and (iii) are not added separately. Rather, a salt of the sweetener derived from aspartic acid with a strong acid such as, for example, the APM.HCl salt, is used instead. This is preferably done using a quantity which is above the solubility limit of that salt. Subsequently, component (ii) is added, following which the components then present in the system are allowed to react for at least one minute to yield the desired sweetening salt. Conversely, it is also possible to first supply component (ii), after which the strong —salt of the sweetener derived from aspartic acid is added with a strong acid. If this embodiment is carried out in an aqueous environment, a 'slurry conversion process' is preferably used, which means that concentrations are used which are at least higher than 3.5 wt.%, but preferably much higher, for example higher than 10 wt.%, and even higher than 30 wt.%, for example 50 wt.%.

It is noted that a process disclosed in CA-A-1027113, in so far as it may be carried out in an aqueous environment, may have similarity with the above described specific and particularly suitable embodiment, but certainly cannot be equated with it. According to this Canadian patent specification, the process is carried out in an aqueous environment and should be carried out at low concentrations, presumably up to max. 2.5 wt.%, because all reagents must be in solution. Furthermore, the required solvent removal in this economically unattractive process leads to an end product that contains less than 90% of the desired sweetening salt. This prior process is, therefore, less suitable the process of the present invention.

In another suitable embodiment of the present invention, the salt of the organic sweetening acid used as a component (ii) is prepared in situ by reacting the organic sweetening acid with a base. Suitable bases are ammonium and/or alkali (alkaline earth) metal hydroxides as well as primary, secondary and tertiary amines, and ammonia.

The process according to the invention can, in principle, be carried out at any suitable temperature in the range from −20 to +90° C., provided that the system remains liquid and stirrable. At too low a temperature, there is a risk of freezing in an aqueous environment, whereas at too high a temperature decomposition of the starting materials and the products, for example by ester hydrolysis, may take place to a serious extent. If the process is carried out entirely at ambient temperature, good results are obtained, also with regards to the thermal stability and the low moisture content of the solid product eventually obtained. Step (b) of the process is, however, preferably carried out at elevated temperature, in particular in the range from 40° C. to 70° C., after which the resulting system is gradually cooled to a temperature in the 0–20° C. range. According to this embodiment, a sweetening salt having excellent filtration properties and good handling properties is eventually obtained, and particularly so when effecting the conversion in an aqueous medium.

If desired, the sweetening salt eventually obtained in the process according to the invention can, after separation, subsequently be washed and dried in a known manner. After that, it is also possible to effect further recrystallization and/or further purification, also in a known manner. A highly suitable form of drying of the sweetening salt is spray-drying. Depending on the choice of the liquid medium, separation of inorganic salt is not even necessary beforehand.

The invention also relates to novel sweetening salts, consisting of (e.g. formed from) two sweetener components: a sweetener derived from aspartic acid and an organic acid which corresponds to an intense sweetener not derived from aspartic acid. The novel sweetening salts feature good resistance to degradation, i.e. less than 0.5%, degradation upon 60 minutes' heating at 120° C., or less than 0.5% degradation upon 70 hours' heating at 70° C. The novel sweetening salts also feature thermal stability and a moisture content <0.5 wt.%, in particular a moisture content <0.25 wt.%. These novel sweetening salts are obtainable when the process according to the invention is carried out in water as a liquid medium. It has, surprisingly, been found that such sweetening salts obtained from water have good thermal stability and can simply be obtained with a moisture content that, in comparison with other known sweeteners, is often low, <0.5 wt.%, in particular <0.2 wt.%, and often even <0.15 wt.%. Good thermal stability in this context means that the products obtained do not show more than 0.5 wt.% decomposition when heated at 120° C. for one hour (respectively at 70° C. for 70 hours). If the decomposition occurring upon heating at 140° C. for one hour does not exceed 0.5 wt.%, the thermal stability can be said to be very good.

We have therefore discovered and demonstrated that with decreasing moisture content, a sweetening salt is obtained which exhibits better thermal stability. Better thermal stability is particularly advantageous when the novel sweetening salts are used in, for example, confectionery products.

Figure 1:
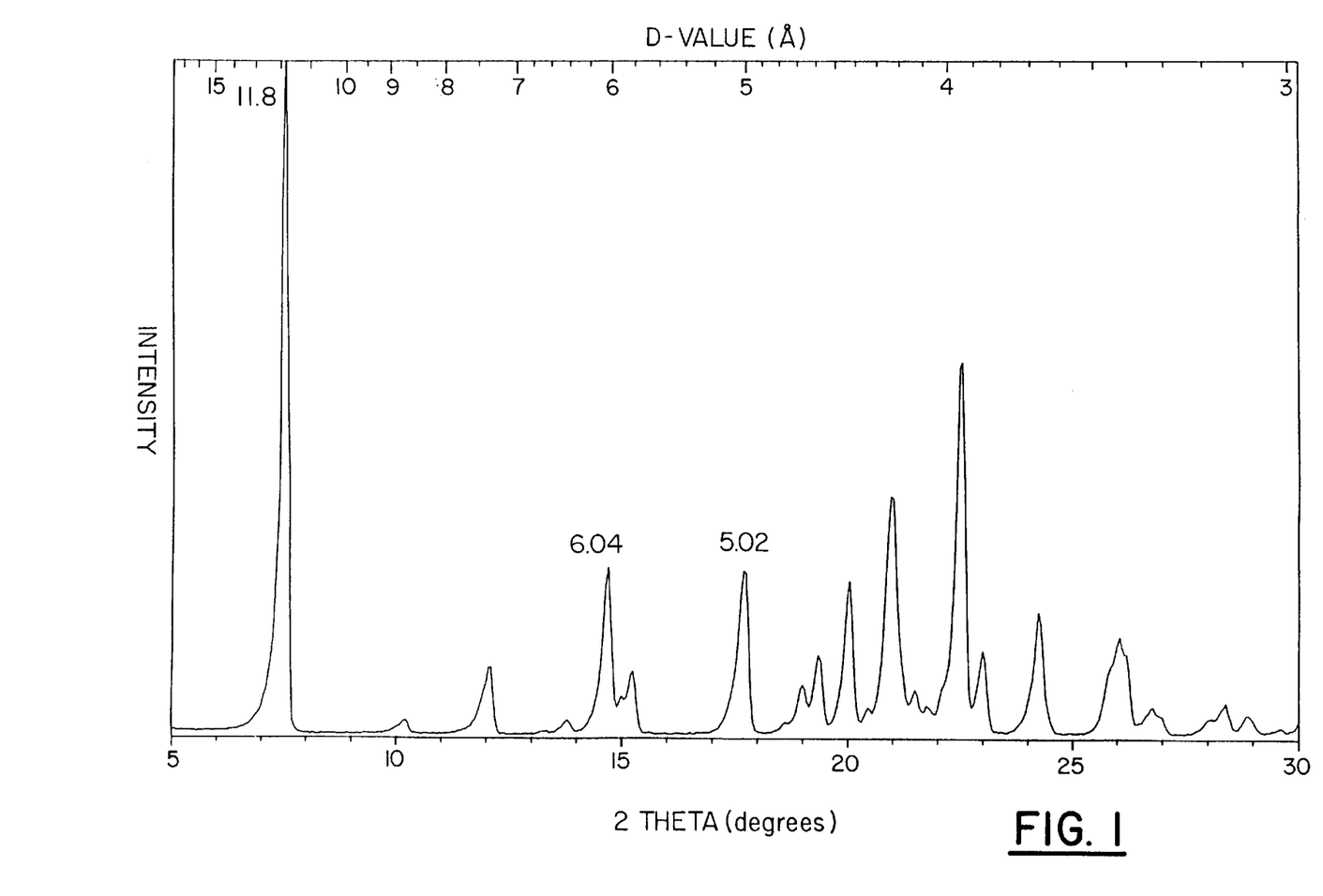
FIG. 1 is an x-ray diffraction pattern for a novel crystal modification of the sweetening salts of aspartame and acesulfamic acid.
Figure 2:
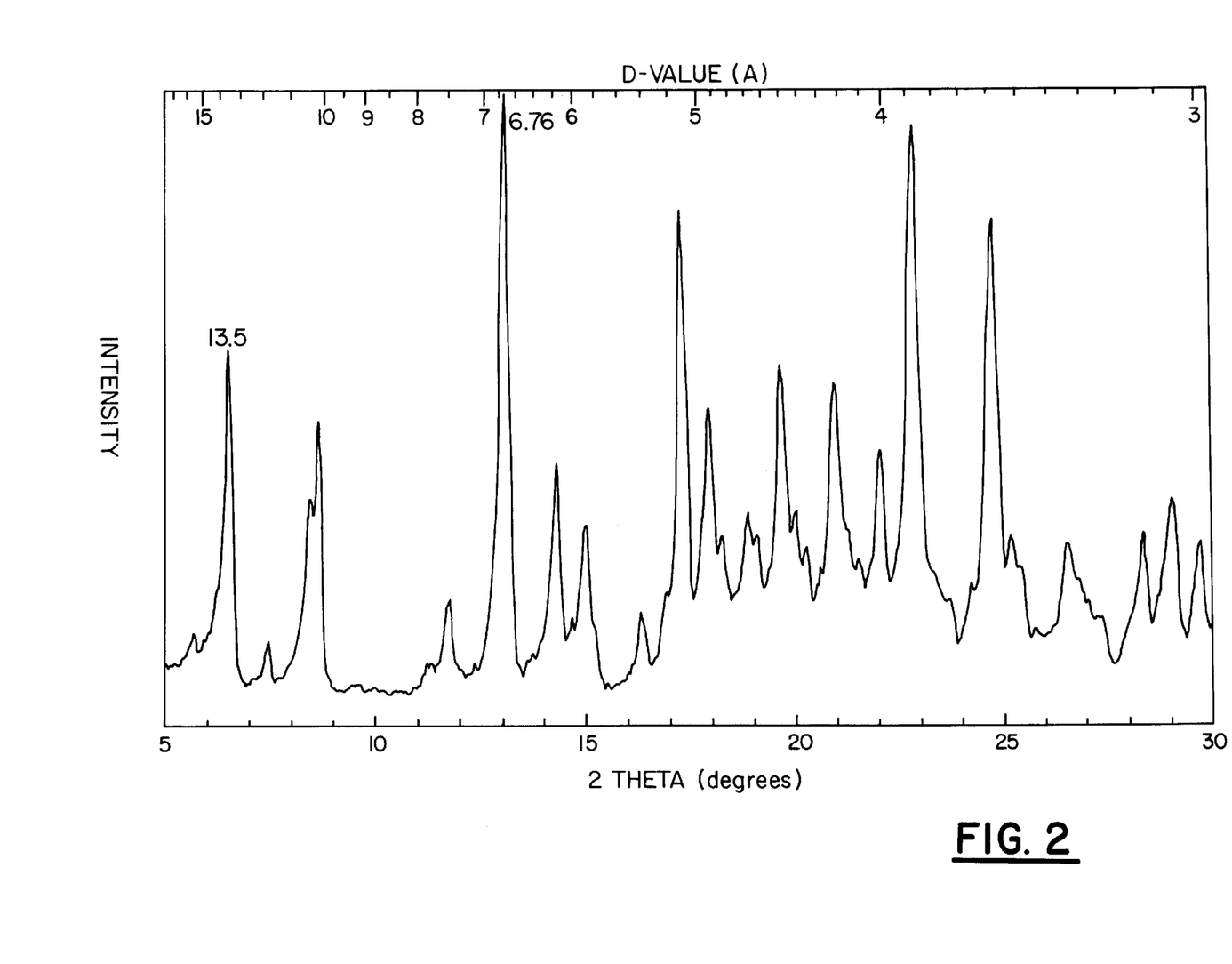
FIG. 2 is an x-ray diffraction pattern of the salt of aspartame and acesulfamic acid obtained according to ES-A-8604766.

The present invention particularly relates also to a new crystal modification of the sweetening salts formed from aspartame and acesulfamic acid. The X-ray diffraction pattern for this new crystal modification is shown in FIG. 1. It is noted, incidentally, that the ratios between the intensities of the diffraction lines may differ without this meaning that a different crystal modification is involved. For the sake of comparison, FIG. 2 presents the X-ray diffraction pattern of the salt in question as would have been obtained upon application of the process according to ES-A-8604766. This is 10 explained in further detail by the examples and comparative examples in this patent application. The X-ray diffraction pattern of the new crystal modification is distinguished especially by characteristic X-ray diffraction lines at D-values of about 11.8, 6.04 and 5.02, while there are no intense lines at D-values of 13.5 and 6.76 (measured via X-ray diffractometry using Cu-K$_\alpha$ radiation).

It is noted that the diffractograms of FIGS. 1 and 2 are represented in a form in which, in particular, the characteristic diffraction lines (2Theta; 2θ) can easily be read. The D-values can simply be derived from the values of 2θ according to the following formula, based on Bragg's law:

$$D=\lambda*(2sin\theta)^{-1}$$

where θ=1.5418 Å (Cu-K$_\alpha$ radiation).

For the diffraction lines indicated by D-values it is conveniently noted that in FIGS. 1 and 2 they are present and absent, respectively, at 2θ positions of, respectively:

| D | = | 11.8 | 2θ = 7.48 |
|---|---|------|-----------|
|   |   | 6.04 | 2θ = 14.65 |
|   |   | 5.02 | 2θ = 17.65 |
|   |   | 13.5 | 2θ = 6.64 |
|   |   | 6.76 | 2θ = 13.08 |

In particular when the process is carried out in an aqueous environment, novel sweetening salts are obtained with good thermal stability, high purity and low moisture content. The good thermal stability, high purity and the low moisture content have proven to be an important and unexpected advantage as regards the broad applicability of the products obtained.

The present invention now offers very good potential applications for several sweetening salts consisting of a sweetener derived from aspartic acid and an organic sweetening acid corresponding to a sweetener not derived from aspartic acid. The invention therefore also relates to the use of these sweetening salts in foodstuff compositions, confectionery products, sweets, chewing gums, et cetera. In particular, the present invention includes the use of a new crystal modification of the sweetening salt of aspartame and acesulfamic acid in such products. If desired, the sweetening salts are applied in the form of preparations or in a mixture with other components, or to influence the so-called sweetness release, are coated with a hydrophobic coating.

The sweetening salts according to the present invention can be granulated. For example, an excellent granulated product is obtainable via wet granulation after addition of about 30–35% water. The sweetening salts are also eminently suitable for compression to tablets. Tableting can be effected, for instance, via direct compression of the salt with the other tablet components. Tableting can also be effected, by subjecting a spray-dried composition of the sweetening salt with, for example, lactose to direct compression with the other components.

The resulting sweetening salts according to the present invention have several advantages. On a weight basis, the products obtainable have a very high sweetening power in comparison with mixtures composed of the individual sweetening components, or with the individual sweetener components themselves. This may be attributed to the low residual moisture content of the dried products which are obtained, as well as to the synergy between the sweet components of the salt. This is particularly the case with products obtainable via the embodiment in which the inorganic salt formed is removed prior to recovery of the sweetening salt. In this respect it is also important that the sweetening salts according to the invention do not contain any alkali (alkaline earth) metal—which on a weight basis does not or hardly contributes to the sweetening power. Most of the individual compounds (i) and (ii), and in particular the latter ones, or their alkali (alkaline earth) metal salts exhibit hygroscopic properties. It is therefore usually hardly possible to obtain those individual components in a simple manner with such a low residual moisture content. For example, saccharin-Na and cyclamate-Ca usually have a moisture content of up to 15% and up to 9%, respectively. In contrast, the sweetening salts that are obtained according to the present invention are not hygroscopic. If no further inorganic salt is present, the sweetening power per gram of product of the present salts is therefore significant, viz. for example at least 10–15% higher than for an equivalent quantity of product made by blending the individual components. In dry form the present salts exhibit good thermal stability at temperatures of 70°–80° C. and higher, and certainly up to 110°–140° C., which is important for so-called 'baking applications'. This thermal stability is expressible particularly in terms of higher retention of sweetening power, and is much better than that exhibited by a sweetener derived 100% from aspartic acid, for example, APM. The sweetness quality of the present salts in solution is also more balanced than that of equi-sweet solutions based on a sweetener derived 100% from aspartic acid, for example APM. The higher dissolving rate of the present salts represents an advantage in various applications, both in water and in buffered systems. This advantage can be enhanced by making use of differences in the dissolution rate, et cetera, depending on the particle size distribution of the salt selected. Furthermore, the salts, in solid form, offer additional advantages, compared with the virtual 1:1 blends of the components. All individual particles of the present salts, in solid form, exhibit the same taste profile and no segregation of the constituent components can take place. Therefore, fluctuations in taste perception will not occur, with the present salts, when samples are taken randomly. This is particularly important in applications such as chewing gums, sweets and powder mixtures.

The density of the sweetening salts according to the invention is generally virtually the same as that of the sweetener derived from aspartic acid that is used as starting material (i). Incidentally, the density of the latter is usually considerably lower than the density of the salts of the organic acid, for example potassium salts, that are also used as starting materials (ii). Consequently, the presence, if any, of an excess of the sweetener derived from aspartic acid in the residual solid product is not prone to segregation. However, any segregation effects can be reduced by suitably selecting the particle size distribution. The salts are generally particularly suitable for use in powder mixtures.

In a special embodiment, the sweetness release of the salts can be influenced as desired by providing the salts with a coating. The coating is a means by which the diffusion of water into the sweetener can be retarded. The coating can be hydrophobic. The salts to be coated can, if desired, be in a predetermined or previously prepared particle size distribution. Several exemplary coating materials are edible fats of vegetable or animal origin, mono-di-, and triglycerides, fatty acids and hydrogenated derivatives of the above-mentioned products, lipoproteins as well as natural or synthetic waxes, such as bees-wax or paraffins or polyethylene waxes.

EXAMPLES

The following non-limiting Examples (experiments) and Comparative Examples (comparative experiments) further described the present invention.

The following techniques were used in the Examples or Comparative Examples.

a. The chemical purity of the sweetening salts obtained was determined by means of high-pressure liquid chromatography (hpic) using a so-called reversed-phase column. Approximately 0.002 molar solutions of the salts were prepared in a pH 4.0 buffer of 4% tetrabutyl ammonium hydroxide and phosphoric acid in water. An 80/20 (v/v) mixture of water and acetonitrile was used as the eluent. The APM content was determined spectrophotometrically at 210 nm, and the saccharinate or acesulfamate content was likewise determined at 227 nm. The accuracy of this method is ±2%. For a number of products a $^1$H-NMR was also recorded (200 MHz; Bruker) for further characterization purposes.

b. The moisture content of the products obtained was determined by means of the Karl-Fischer water determination.

c. The dissolution rate was found through spectrophotometric determination of the dissolution curve, by introducing 0.1 wt.% of the product (or a screen fraction thereof at 23° C. into a pH 5.0 buffer (Merck titrisol, pH 5.0, in 1 liter of Milli-Q water) whilst stirring continuously.

d. Thermal stability tests were conducted by allowing samples of a relevant product to stand for the indicated times in an open dish placed in a thermostatted oven at the relevant temperature, and to determine, via hplc, the concentrations of possible decomposition products such as, in the case of analysis of aspartame salts, diketopiperazine (DKP) and aspartyl-phenylalanine (AP) in the initial and the final sample.

e. X-ray diffraction patterns were recorded under laboratory conditions (using a step scan from 5° to 30°

(2Theta; 2θ) with a step size of 0.050 and a counter time of 1 second per data point) with a Philips goniometer (PW 1820) with Bragg-Brentano geometry, mounted on a Philips generator (PW 1730). Cu-K$_\alpha$ radiation (Ni filter, 40 kV-50 mA, LFF) with a graphite monochromator in the diffracted beam was used.

Divergence and scatter slots were each 10°, and the receiving slot was 0.2 mm. The D-values can simply be derived from the values of 2θ according to the following formula, which is based on Bragg's law:

$$D=\lambda*(2sin\theta)^{-1}$$

where λ=1.5418 Å (Cu-K$_\alpha$ radiation).

If D is higher than 10 Å, the accuracy of the D-values given is 0.1 Å. The accuracy is stated in 0.01 Å for D-values lower than 10 Å.

The following abbreviations have the respective assigned meanings:

APM: aspartame
SacNa/SacK: sodium/potassium saccharinate
SacH: saccharinic acid
CycNa/CycH: sodium cyclamate/cyclamic acid
AceK: potassium acesulfamate
MTBE: methyl-t-butylether Experiment 1 (1a.–b.)

These experiments concern the preparation of salts of APM and SacH and CycH, respectively.

Exp. 1a.

A 500 ml beaker provided with a stirrer was successively charged, at room temperature, with 250 ml of water, 30.4 g of APM (0.10 mole; 3 wt.% H$_2$O) and 21.0 g of SacNa (0.10 mole). In 2 minutes 10 g of a 37% solution of HCl in water (0.10 mole) was added to the resulting slurry, which was meanwhile being stirred. Initially, a clear solution was obtained. Stirring was continued for 30 minutes, and a voluminous white precipitate formed. The precipitate was filtered off over a Buchner filter and washed with a small quantity of cold water of 5° C. and subsequently dried overnight in a vacuum stove at 40° C. 40.1 g of white product was obtained, which was unambiguously characterized via $^1$H-NMR as the 1:1 salt of APM and SacH. The moisture content was 0.03%; the APM and saccharinate contents were found to be 60% and 39%, respectively (theoretical values: 62 and 38%). The quantity of product obtained corresponds to 0.084 mole, which implies the yield of isolated product is 84%. X-ray diffractometry on this product yielded the same diffraction pattern as found for the products of comparative experiments 1A. and 1B. and experiment 4B, respectively.

Exp. 1b.

Analogously to the method of experiment 1 a., 30.4 g of APM, 21.0 g of CycNa and (in 2 minutes) 10.0 g of a 37% solution of HCl in water were successively added to 200 ml of water, which was followed by stirring for 30 minutes. A voluminous slurry was obtained only after cooling down to 0C. This slurry was filtered off at 0° C. and washed with a small quantity of ice water, after which the resulting product was dried overnight in a vacuum stove at 40° C. 25.0 g of dried product (moisture content 0.16%) was obtained, which was unambiguously characterized according to $^1$H-NMR as the 1:1 salt of APM and CycH. This corresponds to an isolated yield of 53%. This value is relatively low in connection with the high solubility of the sweetening salt.

Experiment 2

This experiment concerns the preparation of the salt of APM and acesulfamic acid.

Exp. 2a.–g.

Experiments 2a. through 2g. concern the order of the additions.

Exp. 2a.

Analogously to the method of experiment 1a., 250 ml of water, 30.4 g of APM (0.10 mole) and 21.0 g of AceK (0.10 mole) were successively added to the beaker at room temperature. In 2 minutes 10 g of a 37% solution of HCl in water (0.10 mole) was added to the slurry thus obtained, which was meanwhile being stirred. Initially a clear solution was obtained. Stirring was continued for 30 minutes, upon which a voluminous white precipitate formed. The precipitate was filtered off over a Buchner filter and washed with a small quantity of cold water of 5° C. and subsequently dried overnight in a vacuum stove at 40° C. 40.2 g of white product was obtained, which was unambiguously characterized via $^1$H-NMR as the 1:1 salt of APM and acesulfamic acid. The moisture content was 0.11%; the APM content and the acesulfamate content were found to be 62% and 35%, respectively (theoretical values: 64 and 36%). The quantity of product obtained corresponds to 0.088 mole, which implies a yield of 88%.

Exp. 2b.–2g

Experiment 2a. was repeated a few times, though the order in which the reagents were added was changed. The orders of addition were as follows: (2b.) water, AceK, APM, HCl; (2c.) water, HCl, APM, AceK; (2d.) water, APM, HCl, AceK; (2e.) water, AceK, HCl, APM; (2f.) water, mixture of APM +AceK, HCl. In all these experiments the HCl (as a 37% solution in water) was dosed in 2 minutes. In all these cases virtually identical results were achieved. The same happened when instead of solid APM use was made of a so-called wet cake, with a moisture content of 65%, formed after centrifuging of the wet crystal mass during the APM production process (2g.). Exp. 2e., for that matter, was also repeated at a higher slurry concentration (see Exp. 2l.).

Exp. 2h.–j

Experiments 2h. to 2j. concern the concentration of strong acid.

Experiment 2a. was repeated a few times using different concentrations of the aqueous hydrochloric acid solution, viz. 73 g of 5% HCl (2h.), 37 g of 10% HCl (2i.) and 18.5 g of 20% HCl (2j.), i.e. each time with 0.10 mole HCl. In all these cases virtually identical results were achieved.

Exp. 2k

Experiment 2k. concerns the nature of the strong acid.

The process of Experiment 2a. was also repeated using phosphoric acid addition (11.6 g of an 85% aqueous solution) instead of HCl addition, the phosphoric acid being added in 10 minutes, followed by stirring for 10 minutes before the resulting slurry was filtered, washed and dried. During stirring slurry was constantly present. 38.9 g of white crystalline product was obtained (0.085 mole), which was characterized by means of $^1$H-NMR as being the 1:1 salt; the yield therefore was 85%. The purity was >98%, the moisture content 0.10%.

Exp. 21

Experiment 21. concerns the slurry concentration.

Experiment 2e. was also carried out, partly at a somewhat elevated temperature, at a solids content at the end of the reaction of about 40%. In the order of addition 50 g of water, 10 g of 37% HCl in water, 21.0 g of AceK and 30.4 g of APM. The APM was added in 5 portions of 2 g each at room temperature (in 5 minutes), and subsequently, while the temperature of the entire mixture was gradually being raised to 50° C., also in portions of about 2 g (in 15 minutes) until all APM had been added. Post-stirring was applied for 30 minutes, and then the material was cooled down to room temperature in 30 minutes, following which, after the usual upgrading treatment, 43.0 g (94%, moisture content 0.07%) of the desired 1:1 salt was obtained.

Experiment 3 (3a.–d. and 3a')

These experiments concern use of various liquid media.

Exp. 3a

The process of Experiment 2a. was repeated in 250 ml of methanol instead of 250 ml of water. After the addition of the 37% aqueous HCl a clear solution formed, which was stirred for 30 minutes, upon which a white KCl precipitate formed. After this precipitate had been filtered off, the mother liquor was evaporated to dryness in a lukewarm water bath using the rotavapor and subsequently placed overnight in a vacuum stove at 40° C. 45.2 g of a white solid was obtained, which was identified, via $^1$H-NMR, as the 1:1 salt of APM and acesulfamic acid (99% yield). The moisture content was 2.5%; the APM content and the acesulfamate content were found to be 62% and 33%, respectively (theoretical values: 64 and 36%).

Exp. 3a. was also carried out without intermediate removal of the white KCl precipitate (Exp. 3a.'). In this experiment drying in the vacuum stove yielded 53.3 g of a white solid having a moisture content of 0.5%; the APM content and the acesulfamate content were found to be 54% and 31%, respectively (theoretical values: 55% and 31%).

Exp. 3b 37.0 g of tri-(n-butyl) ammonium saccharinate (0.10 mole) was dissolved at room temperature in 500 ml of an 80/20 (v/v) mixture of MTBE and methanol. Subsequently 30.4 g of APM was added, so that a slurry was obtained, and 9.5 g of a 40% methanolic solution of HCl (0.10 mole) was added in 2 minutes. The slurry system present was subsequently stirred for one hour. The solid product obtained was separated by filtration and washed with MTBE before being dried under vacuum at 40° C., yielding 35.8 g (i.e. a yield of 75%) of the 1:1 salt of APM and saccharinate, its purity being >95%. No presence of residual tri-(n-butyl)-ammonium salt or solvent residues could be established via $^1$H-NMR. The moisture content was 0.27%.

Exp. 3c

At room temperature 2.35 g of alitame (7 mmoles), 0.65 g of a 40% solution of HCl in methanol (7 mmoles; in 2 minutes) and 1.65 g of SacK (7 mmoles) were successively added to 100 ml of ethanol, yielding a slurry. This slurry was stirred for 1 hour, upon which KCl formed as precipitate and the other components went into solution. After the solid KCl formed had been filtered off, the mother liquor was fully evaporated using the rotavapor, the residual solid material being dried further overnight in a vacuum stove at 40° C. 3.20 g (6.21 mmoles; 88% yield) of solid material remained, which was characterized as being the 1:1 salt of alitame and saccharin by means of $^1$H-NMR.

Exp. 3d

At room temperature 1.67 g of alitame (5 mmoles), 1.05 g of AceK (5 mmoles) and 0.48 g of a 40% solution of HCl in methanol (5 mmoles; in 2 minutes) were successively added to 50 ml of ethanol, yielding a slurry. This slurry was stirred for 1 hour, upon which KCl formed as precipitate and the other components went into solution. After the solid KCl formed had been filtered off, the mother liquor was fully evaporated using the rotavapor, the residual solid material being dried further overnight in a vacuum stove at 40° C. 2.30 g (4.65 mmoles; 93% yield) of solid material remained, which was characterized as being the 1:1 salt of alitame and acesulfamic acid by means of $^1$H-NMR.

Experiment 4 (4a.–c.)

These experiments concern the addition of strong acid.

Exp. 4a.

To 2 liters of water at 20° C. were successively added 608 g of APM and 410 g of AceK (2.0 moles each), after which the temperature of the resulting slurry was adjusted to 50° C. and 370 g of 20% HCl in water was added in 30 minutes while the slurry was being stirred. The slurry, which had initially been rather voluminous, changed into a less voluminous slurry. At the end of the HCl addition the slurry obtained was cooled down to 10° C. in about 30 minutes, via indirect heat transfer using a 0° C. cooling medium, and filtered off. The resulting crystalline mass was washed with a minimal quantity of ice water and dried under vacuum at 40° C. Thus, in total 820 g (i.e. a 90% yield) of a white product was obtained, which according to $^1$H-NMR consisted entirely of the 1:1 salt of APM and acesulfamic acid, with a purity >99%. The moisture content was 0.12%. The product was further characterized by means of an X-ray diffraction pattern as shown in FIG. 1. This crystal modification of the APM-acesulfamic acidic salt is new, and differs strongly from that which is obtained on application of the process as described in Comparative Experiments 1C. and 1D. (see also FIG. 2). Products such as obtained in Experiments 2a.–21. have the same crystal modification as that belonging to FIG. 1. X-ray diffractometry in all cases proved that the products had diffraction lines at D-values of about 11.8, 6.04 and 5.02, but not at 13.5 and 6.76.

Exp. 4b.

30.4 g of APM and 21.0 g of SacNa (each 0.10 mole) were successively added to 200 ml water of 20° C., following which the temperature of the resulting slurry was raised to 60° C. and 19 g of 20% HCl (0.10 mole) was added in 30 minutes with stirring. The slurry, which had initially been rather voluminous, changed into a thinner slurry. At the end of the HCl addition the slurry obtained was cooled down to 10° C. in about 30 minutes, via indirect heat transfer using a 0° C. cooling medium, and filtered off. The resulting crystalline mass was washed with a minimal quantity of ice water and dried under vacuum at 50° C. Thus, in total 39.1 g (i.e. a 82% yield; moisture content 0.04%) of a white, crystalline product was obtained, which according to $^1$H-NMR consisted entirely of the 1:1 salt of APM and saccharin, with a purity >98%. The moisture content was 0.05%. The product was also analyzed by recording an X-ray diffraction pattern; however this diffraction pattern did not differ from that obtained by application of the state-of-the-art process as described in Comparative Experiments 1A. and 1B.

Exp. 4c

Experiment 2h. was repeated, but this time the addition of the 73 g of 5% HCl solution in water took place gradually in 1 hour (rather than in 2 minutes). A slurry with good filtering properties was obtained, from which, after the treatment described above, 38.0 g (83% yield) of white product was obtained, which was unambiguously characterized by means of $^1$H-NMR as being the 1:1 salt of APM and acesulfamic acid. The moisture content was 0.04%; the APM content and the acesulfamate content were found to be 63% and 35%, respectively (theoretical values: 64% and 36%). X-ray diffractometry showed that the product exhibited diffraction lines at D-values of about 11.8, 6.04 and 5.02, but not at 13.5 and 6.76.

Experiment 5 (5a.–b.)

Experiments 5a.–5b. concern the ratio of starting materials.

Exp. 5a.

Analogously to the process of experiment 2a., 250 ml of water, 15.2 g of APM (0.05 mole) and 21.0 g of AceK (0.10 mole) were successively added to the beaker at room temperature. In 2 minutes 5 g of a 37% solution of HCl in water (0.05 mole) was added to the slurry thus obtained, which was meanwhile being stirred. The experiment further proceeded as in experiment 2a. 19.0 g (83% yield) of white product, with a moisture content of 0.09%, was obtained, which was characterized via $^1$H-NMR as being the 1:1 salt of APM and acesulfamic acid. The excess AceK remained behind in the filtrate.

Exp. 5b

In a similar manner an experiment was conducted using again different quantities of starting materials, notably 30.4 g of APM (0.10 mole), 10.5 g of AceK (0.05 mole) and 10 g of 37% HCl (0.10 mole). 18.3 g (80% yield) of the 1:1 salt of APM and acesulfamic acid was obtained.

Experiment 6

Experiment 6 concerns the process on the basis of 2 salts.

34.0 g of APM.HCl was added at room temperature to 200 ml of water, yielding a slurry. Next, 21.0 g of AceK was added in 10 minutes with stirring, this being done in 10 portions of 2.1 g each. Stirring was continued for another hour. After filtration, washing and drying of the resulting solid product, 38.4 g (84% yield) of the 1:1 salt of APM and acesulfamic acid was obtained ($^1$H-NMR; >98% pure), its moisture content being 0.15%.

Experiment 7

Experiment 7 concerns a product with excess APM.

The process of experiment 2a was repeated, this time with a quantity of APM that was twice as large, viz. 60.8 g of APM, all other quantities and activities being the same. In this experiment slurry remained present during the entire stirring period. After filtration and the customary treatment, 76.3 g of solid material was obtained, which according to $^1$H-NMR contained about twice as much APM as acesulfamate.

Comparative experiments 1A.–D.

These Comparative Experiments are in conformity with ES-A-8604766.

Examples 1 and 2 of ES-A-8604766 were repeated (Comparat(Comparative Experiments 1A. and 1B., respectively) using the quantities of SacH and APM in cmole there indicated, as well as by analogy, though not described in ES-A-8604766, using acesulfamic acid (obtained by rapidly upgrading a slurry of AceK with HCl in methanol by first filtering off the KCl formed and then evaporating the filtrate using the rotavapor) rather than SacH (Comparative Experiments 1C. and 1D., respectively).

Comp. Exp. 1A.

In 200 ml of methanol 9.15 g of SacH (5 cmoles) was dissolved to which 15.2 g of APM (5 cmoles) was added, yielding a slurry which had to be heated to 45° C (rather than 40°–41° C. as described) to obtain a clear solution. Rotavapor evaporation at 36°–37° C. (35 minutes) produced 24.3 g of a white substance, which was unambiguously characterized via $^1$H-NMR as being the 1:1 salt of APM and SacH; its melting point was 203° C. The quantity of product obtained corresponds to roughly 5 cmoles, which means the isolated product yield is almost 100%. X-ray diffractometry on this product produced a similar diffraction pattern as found for the products of, for example, Experiments 1a. and 4b.

Comp. Exp. 1B.

18.3 g of SacH (10 cmoles) was dissolved in 450 ml of methanol of 25° C. and then 30.4 g of APM (10 cmoles) was added, followed by rinsing using 50 ml of methanol, upon which a white slurry was obtained which, after 15 minutes' stirring, was heated to 45° C. in 6 minutes so that a solution was obtained. The solution was subsequently cooled down to 26° C. in 6 minutes and then evaporated at 36° C. using the rotavapor (in 40 minutes). This yielded 38.6 g of a white solid, which was unambiguously characterized via $^1$H-NMR as being the 1:1 salt of APM and SacH; its melting point was 203° C. The quantity of product obtained corresponds to roughly 10 cmoles, which means the isolated product yield is almost 100%. X-ray diffractometry on this product produced a similar diffraction pattern as found in Comparative Experiment 1A. It is noted that in the Comparative Experiments 1A. and 1 B. no differences in the end product formed could be observed, although ES-A-8604677 suggests otherwise.

Comp. Exp. 1C.

Using a method analogous to that of Comparative Experiment 1A an experiment was carried out using 8.2 g of acesulfamic acid (5 cmoles) instead of SacH. The solid white product eventually obtained weighed 23.1 g and was unambiguously characterized as being the 1:1 salt of APM and acesulfamic acid by means of $^1$H-NMR. The moisture content was 0.76%; the APM content and the acesulfamate content were found to be 62% and 35%, respectively (theoretical values: 64% and 36%). The quantity of product obtained corresponds to about 5 cmoles, which means the yield of isolated product was almost 100%. X-ray diffractometry on this product yielded a diffraction pattern as shown in FIG. 2. This is clearly a different crystal modification than in the products of, for example, Experiments 4a. and 2a.–2k.

Comp. Exp. 1D.

Using a method analogous to that of Comparative Experiment 1B. an experiment was carried out using 16.4 g of acesulfamic acid (10 cmoles) instead of SacH. The solid white product eventually obtained weighed 46.4 g and was unambiguously characterized as being the 1:1 salt of APM and acesulfamic acid by means of $^1$H-NMR. The moisture content was 0.89%; the APM content and the acesulfamate content were found to be 63% and 34%, respectively (theoretical values: 64% and 36%). The quantity of product obtained corresponds to about 10 cmoles, which means the yield of isolated product was about 100%. X-ray diffractometry on this product yielded a diffraction pattern that is comparable to that of FIG. 2.

Other experimental results

A number of the products obtained in the above-mentioned experiments and comparative experiments were subjected to further analysis of characterization. The following values were determined: (a) thermal stability (at 70° C. and/or at 120° C.) and (b) dissolution rate. By way of comparison the same was done for a number of reference substances. As regards the thermal stability of the APM containing substances, attention was paid in particular to the increase in the diketopiperazine decomposition product (DKP) in wt.% relative to the dry product. The results are summarized in the following table. It was also established that the salts included in the table are not hygroscopic. These results clearly prove that the products obtained via the process of the invention and the new crystal modification of the salt of APM and acesulfamic acid have particularly good properties.

| Experiment/ Comparative experiment or reference substance | moisture content (wt. %) | DKP content (wt. %) | Increase in DKP content (wt. %) 70 hours, 70° C. | Increase in DKP content (wt. %) 1 hour, 120° C. | Dissolution rate (minutes) |
|---|---|---|---|---|---|
| exp. 1a. (APM-Sac) | 0.03 | 0.01 | 0 | 0 | 1 |
| exp. 1b. (APM-Cyc) | 0.16 | 0.18 | * | 0.14 i) | * |
| exp. 2a. (APM-Ace) | 0.11 | 0.01 | 0 | 0 | 1 |
| exp. 4a. (APM-Ace) | 0.12 | 0.01 | * | 0 ii) | 1 |
| exp. 4c. (APM-Ace) | 0.04 | 0.01 | 0 | 0 ii) | 1 |
| comp. exp. 1A (APM-Sac) | * | 0.53 | 0 | _ 0 | * |
| comp. exp. 1B (APM-Sac) | * | 0.21 | 0 | _ 0 | * |
| comp. exp. 1C (APM-Ace) | 0.76 | 0.35 | 1.27 iii) | 2.04 iv) | * |
| comp. exp. 1D (APM-Ace) | 0.89 | 0.32 | 0.52 iii) | 2.18 iv) | * |
| APM granulate | 2.30 | 0.18 | 0.75 | 2.09 | 4 **) |
| APM powder (ref) | 2.60 | 0.04 | 0.20 | 2.34 | 2–3 |
| AceH (ref) | * | * | * | degradation v) | * |
| SacH (ref) | * | * | * | stable | * |

Notes to the table:
* not determined
i) pale yellow discolouration; no significant decomposition of the cyclamate part
ii) fully stable, white product
iii) pale yellow; with hplc some degradation of the Ace part can be observed
iv) yellow/yellow-brown colour, with some degradation of the Ace part
v) yellow/orange colour; strong degradation; hydrogen sulphide odour
**) <200 μm fraction (NB: 200–700 μm fraction: 7 minutes)

The present inventions can also be further explained by reference to FIG. 1 which is an X-ray diffraction pattern of the new crystal modification of the salt of APM and acesulfamic acid. This diffraction pattern was made of the product of Experiment 4a. For recording technique, etc., see point e. of the introduction to the experimental part.

That can be compared to FIG. 2 which is an X-ray diffraction pattern of the crystal modification of the salt of APM and acesulfamic acid as would have been obtained upon application of the process according to ES-A-8604766. This diffraction pattern was made of the product of Comparative Experiment 1C. For recording technique, etc., see point e. of the introduction to the experimental part.

We claim:

1. A process conducted in a liquid medium for the preparation of a sweetening salt as the reaction product from two sweetener components, wherein one component is a sweetener derived from aspartic acid and the other component is a derivative of an organic sweetening acid which corresponds to an intense sweetener not derived from aspartic acid, said process comprising the combination of steps of:

(a) forming a liquid system containing a sweetener component derived from aspartic acid and a sweetener component derived from an organic sweetening acid which corresponds to an intense sweetener not derived from aspartic acid by adding to a liquid medium, in any order, components (i), (ii) and (iii):
- (i) the sweetener component derived from aspartic acid,
- (ii) the derivative of an organic sweetening acid which corresponds to an intense sweetener not derived from aspartic acid, and
- (iii) a strong acid whereby the liquid system is obtained, (b) allowing the components then present in the liquid system, optionally with agitation, to react for at least one minute, wherein a reaction mixture containing the sweetening salt is formed; and (c) isolating the sweetening salt from the reaction mixture.

2. The process according to claim 1, wherein said derivative of the organic sweetening acid which corresponds to an intense sweetener not derived from aspartic acid is a salt.

3. The process according to claim 1, wherein at least at the end of step (b), at least 1.0 wt. % of solid material is present in the reaction mixture.

4. The process according to claim 1 or 2, wherein in said process the amount of said sweetener derived from aspartic acid and the amount of said derivative of the organic sweetening acid which corresponds to an intense sweetener not derived from aspartic acid are such that they are applied in a molar ratio in the range of from 0.2:1 to 5:1.

5. The process according to claim 1 or 2, wherein in said process the amount of said sweetener derived from aspartic acid and the amount of said derivative of the organic sweetening acid which corresponds to an intense sweetener not derived from aspartic acid are such that they are applied in a molar ratio in the range from 0.5:1 to 2:1.

6. The process according to claim 1 or 2, wherein in said process the amount of said sweetener derived from aspartic acid and the amount of said derivative of the organic acid which corresponds to an intense sweetener not derived from aspartic acid are such that they are applied in a molar ratio of about 1:1.

7. The process according to claim 1 or 2, wherein said liquid medium is selected from the group consisting of water, a polar organic solvent, an apolar organic solvent, blends of water-miscible organic solvents, blends of water-immiscible solvents, or a mixture of any thereof.

8. The process according to claim 1 or 2, wherein the liquid medium is an aqueous medium.

9. The process according to claim 7, wherein the liquid medium is water.

10. The process according to claim 1 or 2, wherein the strong acid is at least one inorganic strong acid selected from the group consisting of hydrochloric acid, sulphuric acid and phosphoric acid.

11. The process according to claim 10, wherein said strong acid is gaseous hydrochloric acid.

12. The process according to claim 10, wherein in said process a solution of said strong acid is used.

13. The process according to claim 1 or 2, wherein the total molar quantity of $H^+$ of the strong acid is at least equal to 25% of the molar quantity of the sweetener component derived from aspartic acid.

14. The process according to claim 1 or 2, wherein the total molar quantity of $H^+$ of the strong acid is equimolar to the molar quantity of sweetener derived from aspartic acid.

15. The process according to claim 1 or 2, wherein the step (b) further comprises agitating the liquid system.

16. The process according to claim 1 or 2, wherein first at most two of the three components (i), (ii) and (iii) are added to the liquid medium, optionally after first having combined two said two components, and subsequently the remaining component(s) is (are) added to the liquid medium.

17. The process according to claim 16, wherein the subsequent addition is carried out gradually.

18. The process according to claim 16, wherein in said process components (i) and (iii) are added to the liquid medium in the combined form of a strong acid (iii) addition salt of component (i), and said liquid medium is an aqueous medium.

19. A process conducted in a liquid medium for the preparation of a sweetening salt as the reaction product from two sweetener components, wherein one component is a sweetener derived from aspartic acid and the other component is a derivative of an organic sweetening acid which corresponds to an intense sweetener not derived from aspartic acid, said process comprising the combination of steps of:

(a) forming a liquid system containing a sweetener component derived from aspartic acid and a sweetener component derived from an organic sweetening acid which corresponds to an intense sweetener not derived from aspartic acid by combining a liquid medium with components (i), (ii) and (iii):
- (i) the sweetener component derived from aspartic acid,
- (ii) salt of an organic sweetening acid which corresponds to an intense sweetener not derived from aspartic acid, wherein said salt is prepared is situ by allowing the corresponding organic sweetening acid to react with a base, and
- (iii) a strong acid whereby the liquid system is obtained, (b) allowing the components then present in the liquid system, optionally with agitation, to react for at least one minute, wherein a reaction mixture containing the sweetening salt is formed; and (c) isolating the sweetening salt from the reaction mixture.

20. The process according to claim 1 or 19, wherein in step (a) part of said strong acid is added to said liquid medium, and wherein the remainder of said strong acid is gradually added while step (b) proceeds.

21. The process according to claim 1 or 19, wherein step (b) is conducted at an elevated temperature.

22. The process according to claim 21, wherein step (b) is conducted at a temperature in the range of 40° C. to 70° C.

23. The process according to claim 21, wherein said process further comprises subsequently gradually cooling the reaction mixture from step (b) to a temperature in the range of 0° C. to 20° C.

24. The process according to claim 1 or 19, wherein in step (c) said sweetening salt is a precipitate in said reaction medium and said sweetening salt is separated from said reaction medium.

25. The process according to claim 1 or 19, wherein step (c) comprises separating out any inorganic precipitates, and then crystallizing out said sweetening salt from said reaction medium.

26. The process according to claim 1 or 19, wherein said process further comprises the steps of (d) washing the isolated sweetening salt, (e) drying said washed sweetening salt, and, optionally, (f) recrystallizing said dried sweetening salt, and, optionally (g) further purifying said dried sweetening salt or the recrystallized salt.

27. The process according to claim 1 or 19, wherein said derivative of the organic sweetening acid which corresponds to an intense sweetener not derived from aspartic acid is a potassium, sodium, calcium, ammonium, and or secondary or tertiary amine salt.

28. The process according to claim 1 or 19, wherein said sweetener derived from aspartic acid comprises aspartame or alitame.

29. The process according to claim 1 or 19, wherein said derivative of an organic sweetening acid which corresponds to an intense sweetener not derived from aspartic acid comprises acesulfamic acid, saccharinic acid or cyclamic acid.

30. The process according to claim 29, wherein said derivative of said organic sweetening acid which corresponds to an intense sweetener not derived from aspartic acid is a potassium, sodium, calcium, ammonium or secondary or tertiary amine salt of said organic sweetening acid.

31. A sweetening salt which is a reaction product from two sweetener components, wherein one component is a sweetener derived from aspartic acid and the other component is an organic sweetening acid which corresponds to an intense sweetener not derived from aspartic acid, said sweetening salt having less than 0.5% degradation when heated for 60 minutes at 120° C., or less than 0.5% degradation when heated for 70 hours at 70° C., and said sweetening salt having a moisture content of <0.5 wt. %.

32. The sweetening salt according to claim 31, wherein said moisture content is <0.2 wt. %.

33. The sweetening salt according to claim 31, wherein said sweetening salt is a reaction product from aspartame and acesulfamic acid, said sweetening salt being a crystal modification having characteristic X-ray diffraction lines at D-values of about 11.8, 6.04, and 5.02, and said crystal modification being further characterized by the absence of intense lines at D-values of 13.5 and 6.76 (measured by X-ray diffractometry using Cu-$K_\alpha$ radiation).

34. A foodstuff, confectionery product, sweets or chewing gum containing at least one sweetening salt according to claim 36, 32 or 33.

* * * * *